United States Patent
Ghorpade et al.

(10) Patent No.: US 6,388,097 B1
(45) Date of Patent: May 14, 2002

(54) PROCESS FOR THE PREPARATION OF β HYDROXY-δ LACTONE USING NOVEL INTERMEDIATES

(75) Inventors: Sandeep Raghunath Ghorpade; Uttam Ramrao Kalkote; Subhash Prataprao Chavan; Sunil Ramchandra Bhide; Thottappillil Ravindranathan, all of Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/783,748

(22) Filed: Feb. 15, 2001

(51) Int. Cl.[7] .............................. C07F 7/02; C07F 7/08
(52) U.S. Cl. ...................... 549/214; 556/482; 435/123
(58) Field of Search ................................ 549/214, 421; 435/125; 556/482

(56) References Cited

U.S. PATENT DOCUMENTS 4,739,073 A    4/1988    Kathawala ................... 548/406

FOREIGN PATENT DOCUMENTS

WO          9306235          4/1993

OTHER PUBLICATIONS

De Brabander, J.; Kulkarni, B. A.; Garcia–Lopez, R.; Vandewalle, M. 1998 CA 128:167301 (R)–Carvone as chiral template for the synthesis of some polyols.*
De Brabander, J.; Kulkarni, B. A.; Garcia–Lopez, R.; Vandewalle, M. 1997 CA 127:65636 Bryostatin: a novel asymmetric synthesis of the C27–C34 fragment starting from (R)–carvone as chiral template.*
Suemune, Hiroshi; Takahashi, Miho; Maeda, Sachiko; Xie, Zhuo F 1991 CA 114:42336 Asymmetric hydrolysis of cis,cis–5–benzyloxy–1, 3–diacetoxycyclohexane and its application to the synthesis of chiral lactone moiety in compactin.*
Rosen.T., et al. Synthetic and Biological Studies of Cmpactin and Related Compounds.2. Synthesis of the Lactone Moiety of Compactin[1], J. Org. Chem., 1984, 49, 3994–4003.
Tang Jenny, et al. Bakers' Yeast Oxidation of Methyl para-Tolysulfide: Synthesis of a Chiral Intermediate in the Preparation of the Mevinic Acid–Type Hypocholestemic Agents 1995, 51, pp 13217.
Beecher Jean, et al. Oxidation of Methyl P–Tolyl Sulfide With Bakers' Yeast Preparation of a Synthon of the Mevinic Acid–Type Hypocholestemic Agents 1995, 1641–1643.
Brower L. Philip, et al. The Synthesis of (4R–CIS)–1, 1Dimethleth1 6–Cyanomethyl 1–2,2–DImethyl–1, 3–Dioxane–4–Acetate, A Key Intermediate For the Preparation of CI–981,A High Potent, Tissue Selective Inhibitor of HMG–CoA Reductase, 1992,33,2279–82.

Prasad Kapa, et al., A Novel Diastereoselective Synthesis of the Lactone Moiety of Compactin, 1984, 25, 2435–38, H, Suemune, et all. Tet. Asymm.,1990, 1,425–8,M., Canda.M, Tet. ASU,,ETRU 1990, 1,17–20.

Bonini.C, et al., A Remarkable Short Synthesis of Optically Active Mevici Acid Analogue By Biocatalytic Lactonization of Syn–3,5–Dihydroxy Esters[1], 1991, 56, 4050.

Bonini .C, et al., Polyhydroxylated Chiral Building Block By Enztmatic Desymmetrization of Meso 1,3 Syn Diols 1991, 58, 802.

McChague Ray, et al., Enanthioselective Synthesis of the Hydroxy–Lactone Moiety of Acids, 1993, 34, 3785.

Bauer T., et al., Diastereoselective Synthesis of the Lactone Portion of Compactin and Mevinolin, 1996, 7, 1391.

Takano S., A Facile Chiral Synthesis of the Lactone Moiety of Compactin and Mevinolin from (R)–O–Benzlyglcidol, 1989, 539.

Hatakeyama S., et al. Red–Al Promoted Intramolecular Reductive Cleavage of Benzl 4–Hydroxy–2–Butenyl Ether Structures, A Concise Preparation of Polyol Chiral Blocks, 1993,34, 7425.

* cited by examiner

Primary Examiner—Amelia Owens
(74) Attorney, Agent, or Firm—Ladas & Parry

(57) ABSTRACT

The present invention relates to a process for the preparation of optically active 6-hydroxymethyl-4-tert-butyldimethylsilyloxy)-(4S,6R)-tetrahydro-2H-2-pyranone (β Hydroxy δ Lacone) and the compound 3-oxo-5-(tert.butyldimethylsilyloxy-(1S-5S)-cyclohexylacetate having the formula

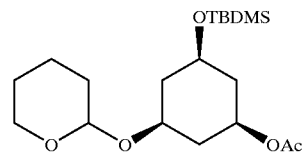

the compound 3-hydroxy-5-(tert,butyldimethylsilyloxy)-(3R,5S)-cyclohexan-1 having the formula

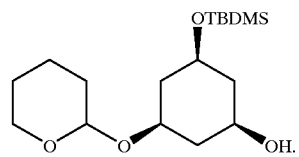

9 Claims, No Drawings

PROCESS FOR THE PREPARATION OF β HYDROXY-δ LACTONE USING NOVEL INTERMEDIATES

This invention relates to a process for the preparation of optically active 6-hydroxymethyl-4-(tert-butyldimethylsilyloxy)-(4S,6R)-tetrahydro-2H-2-pyranone (β Hydroxy-δ-Lactone) having formula 1.

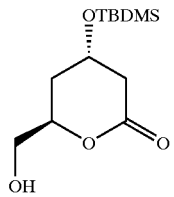

1

More particularly it relates to a process for the preparation of the said compound using compound having formula 5, which was obtained from Cis, cis-3,5-di(methylcarbo

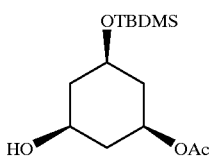

5 nyloxy)cyclohexylacetate having formula 2 by following the earlier patent procedure.

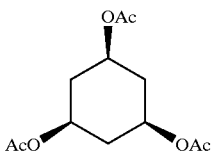

2

Hitherto known processes for the synthesis of β-hydroxy-δ-lactone (1) involves
a) Enzymatic kinetic resolution of racemic β-hydroxy-δ-lactone by transesterification with vinyl acetate in THF using *Chromobacteriun viscosum* lipase as catalyst at 40° C. [Crosby, J. B.; Andrew, J. H.; John, A. L. WO 9306235 A1 CA 119:936292 (1993)]
b) Chemoenzymatic route involving kinetic resolution through lactone formation in ether catalyzed by PPL [Bonini, C.; Pucci, P.; Viggiani, L. *J. Org. Chem.* 1991, 56,4050]
c) Chemoenzymatic route involving enzymatic desymmetrization of intermediate diacetate, followed by chemical conversions. [Bonni, C.; Racioppi, R.; Righi, G.; Viggiani, L. *J. Org. Chem.* 1991, 58, 802]

The prior art processes have following drawbacks:
1. The processes use chemicals such as butyl lithium, lithium aluminum hydride, methoxydiethylborane that are costly and difficult to handle and therefore make the process difficult.
2. All known process are however involves large number of synthetic steps resulting in low over all yields.

The main object of the present invention is to provide a new process for the preparation of β-hydroxy-δ-lactone (1), which obviates the drawbacks of the prior art processes and use cheaper and easily accessible chemicals.

Another object of the present invention is to provide (i) selective Baeyer-Villiger rearrangement of 3-hydroxy-5-t-butyldimethylsilyloxy-1-cyclohexanone (7) with chemical reagent or Baeyer Villiger oxidase and (ii) enantioselective hydrolysis of cis-3-(methylcarbonyloxy)-5-(tert-butyldimethylsilyloxy)cyclohexylacetate with enzyme. (iii) mild enzymatic hydrolysis of 3-oxo-5-(tert.butyldimethylsilyloxy)-(1S, 5S)-cyclohexylacetate (6) wherein β-elimination is suppressed and optical purity is enhanced through kinetic resolution.

DETAILED DESCRIPTION OF THE INVENTION

Accordingly the present invention provides a process for the preparation of 6-Hydroxy methyle-4-(tert-butyl dimethylsilyloxy)-(4R, 6S)-tetra hydro 2H-2-pyranone of formula 1 using novel intermediates which comprises
a) reacting 3-hydroxy-5-(tert.butyldimethylsilyloxy)-(1S, 3R,5R)-cyclohexylacetate having formula 5 in an organic solvent preferably chloroalkanes with chlorochromate of tertiary amines at temperature ranging from 10 to 30° C., quenching the reaction by adding of diethyl ether, filtering the mixture through ceilite and washing with brine, removing the solvent by evaporation, followed by fast column filtration to obtain 3-oxo-5-(tert.butyldimethylsilyloxy)-(1S, 5S)-cyclohexylacetate having formula 6,

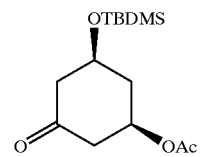

6 b) hydrolysing 3-oxo-5-(tert.butyldimethylsilyloxy)-(1S, 5S)-cyclohexylacetate having formula 6 with lipase enzyme in a buffer having pH range of 5 to 7, at a temperature ranging from 25 to 30° C. for a period ranging between 24 to 48 hr, extracting the mixture with an organic solvent, removing the solvent by evaporation and on column chromatography to obtain 3-hydroxy-5-(tert-butyldimethyl silyloxy)-(3R,5S)-cyclohexan-1-one having formula 7,

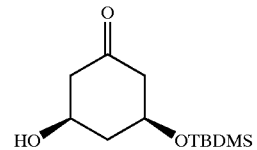

7 c) reacting 3-hydroxy-5-(tert-butyldimethyl silyloxy)-(3R, 5S)-cyclohexan-1-one having formula 7 with m-chloroperbezoic acid at room temperature for the period ranging from 16–24 hours, extracting with organic layer, washing with sodium metabisulphite, brine, drying and on evaporation to obtain 6-hydroxymethyl-4-(tert-butyldimethylsilyloxy)-(4S,6R)-tetrahydro-2H-2-pyranone having formula 1, In another embodiments of the present invention the organic solvent used in steps a–c for the extraction of the product is selected from the group consisting of ethyl acetate, chloroform and dichloromethane.

In another embodiments of the present invention the buffer used in steps b for the reaction is selected from phosphate buffer and citrate buffer.

In another embodiments of the present invention the lipase used in steps b for the reaction is selected from the group consisting of pig procain lipase (PPL), pig liver esterase (PLE) and chicken liver acetone powder (CLAP).

In yet another embodiment of the present invention the enzymatic hydrolysis used in step b is mild and suppresses B-elimination along with enhancement in optical purity.

In yet another embodiment the oxidising agent used is selected from the group consistting of chloroperbenzoic acid, hydrogen peroxide and per acetic acid.

In yet another embodiment the present invention provides a compound 3-oxo-5 (tert.butyldimethylsilyloxy-(1S,5S)-cyclohexylacetate having formula 6

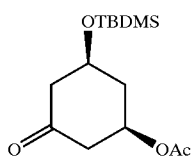

6

In yet another embodiment the present invention provides a compound 3-hydroxy-5-(tert-butyldimethyl silyloxy)-(3R, 5S)-cyclohexane-1-one having formula 7

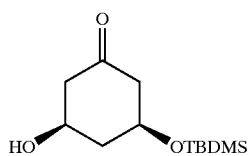

7

The process of the present invention is described herein below with references to the following examples, which are illustrative only and should not be construed to limit the scope of the present invention in any manner.

The novel components having formulae 3 to 5 have been claimed in our co-pending application No. 09/783,749.

EXAMPLE 1

Preparation of cis, cis-3-hydroxy-5-methylcarbonyloxy-cyclohexylacetate (3)

Finely powdered cis, cis-3,5-di(methylcarbonyloxy) cyclohexylacetate 2 (6.5 parts, 25.19 mmol parts) was suspended in 0.1 M sodium phosphate buffer (pH 7) (135 parts) and stirred vigorously. To the stirred suspension Porcine Liver Esterase (0.110 parts) was added and reaction mixture was stirred vigorously at 30° C. for 20 hr. pH of the reaction mixture was monitored at every 2 hrs and was maintained at pH 7 using 1N NaOH solution. After completion of reaction (20 hr), it was extracted with ethyl acetate (2×150 parts). Organic layers were combined and washed with brine, dried on anhydrous sodium sulfate and concentrated under vacuum to yield cis,cis-3-hydroxy-5-methylcarbonyloxycyclohexylacetate 3 yield (4.8 g parts, 88%).

1H NMR(CDCl$_3$): δ1.20–1.58 (qn, 3H), 2.08 (s, 6H), 2.28 (m, 3H), 3.78 (m, 1H), 4.78 (m, 2H)

13C NMR (CDCl$_3$): δ21.15, 36.33, 39.93, 64.83, 67.65, 170.42

IR (KBr): 754.60, 884.15, 1029.29, 1140.34, 1250.00, 1367.64, 1738.92, 2871.17, 2953.14, 3445.47

Mass: Base m/e=96 other m/e: 156, 138, 114, 73, 67, 67, 60, 55

Elemental analysis: calculated for $C_{10}H_{16}O_5$: C, 55.56%; H, 7.40%;. Found: C,55.30%; H,8.00%;.

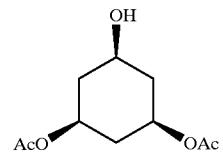

3

EXAMPLE 2

Preparation of cis,cis-3-(methylcarbonyloxy)-5-(tert.butyldimethylsilyloxy)cyclohexylacetate (4)

Cis, cis-3-hydroxy-5-methylcarbonyloxy-cyclohexylacetate (3, 2 parts, 9.26 mmol) and DMAP (0.113 parts, 0.926 mmol) were placed in 100 ml two-necked round bottom flask equipped with dropping funnel and two-way stopcock. It was evacuated and flushed with argon. To it, dry dichloromethane (10 parts) and dry HMPA (2 part) was added and stirred to dissolve. The solution was cooled to −10° C. with stirring. To it, solution of tert-butyldimethylsilyl chloride in 10 part dry dichloromethane was added dropwise while maintaining temperature below 0° C. Reaction mixture was stirred for 15 min and to it dry triethylamine (2.02 parts, 20 mmol) was added dropwise. Reaction mixture was stirred at room temperature for 12 hr. It was then transferred to a separating funnel and washed successively with cold, dil. HCl water, aq. NaHCO$_3$ and then brine. Organic layer was dried on anhydrous sodium sulfate and solvent was removed under vacuum. Residue was purified by flash column chromatography. (eluent 2–4% ethyl acetate in petroleum ether) to yield Cis,cis-3-(methylcarbonyloxy)-5-(tert.butyldimethylsilyloxy) cyclohexylacetate (4, yield 2.85 parts, 90%).

$^1$H NMR (CDCl$_3$): δ0.06(s, 9H), 0.87 (s, 6H), 1.20–1.45 (m, 3H), 2.03 (s, 6H), 2.2 (m, 3H), 3.38 (m, 1H), 4.73 (m, 2H).

$^{13}$C NMR (CDCl$_3$): δ−5.07, 17.61, 25.40, 36.17, 40.40, 65.43, 67.01, 169.64

IR (CHCl$_3$): 758.90, 838.05, 1034.91, 1106.32, 1246.82, 1368.91, 1734.01, 2858.81, 2955.07

Mass: Base m/e=117 other m/e: 273, 213, 171, 159, 129, 117, 97, 79, 75, 57

Elemental analysis: calculated for $C_{26}H_{30}O_5Si$: C, 58.185%; H, 9.10%;. Found: C,58.19%; H,9.50%;.

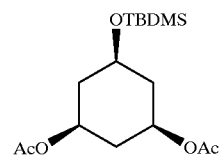

4

EXAMPLE 3

Preparation of 3-hydroxy-5-(tert.butyldimethylsilyloxy)-(1S,3R,5R)-cyclohexyl acetate (5)

Cis, cis-3-(methylcarbonyloxy)-5-(tert.butyldimethylsilyloxy)cyclohexylacetate (4, 5 parts, 147 mmol) was dissolved in tert-butanol (20 parts). To the solution, 0.1 M sodium phosphate buffer (230 parts, pH 8) was added and mixture was stirred vigorously. To the stirred emulsion, Porcine liver esterase (0.150 parts) was added and the mixture was stirred vigorously at 30° C. for 54 hrs. During reaction pH was maintained at 8 using 1N sodium hydroxide solution. Reaction mixture was extracted with ethyl acetate (3×200 parts). Organic layers were combined and washed with brine. It was then dried on anhydrous sodium sulfate and solvent was removed under vacuum. Oily residue contained 3-hydroxy-5-(tert.butyldimethylsilyloxy)-(1S,3R,5R)-cyclohexylacetate 5 along with unreacted 4. Both were separated by flash column chromatography.

Cis,cis-3-(methylcarbonyloxy)-5-(tert.butyldimethylsilyloxy)cyclohexylacetate: (4, 1.07 parts;

3-hydroxy-5-(tert.butyldimethylsilyloxy)-(1S,3R,5R)-cyclohexylacetate: (5, 2.8 parts, 70% based on recovered starting material).

$^1$H NMR (CDCl$_3$): δ0.06 (s, 9H), 0.87 (s, 6H), 1.35–1.60, (m, 3H), 2.06 (s, 3H), 2.15 (m, 3H), 3.7 (m, 2H), 4.75 (m, 1H)

$^{13}$C NMR (CDCl$_3$): δ–4.60, 18.15, 21.38, 25.90, 39.98, 40.31, 43.93, 65.45, 66.40, 68.17, 170.68

IR (CHCl$_3$): 758.43, 838.93, 1049.42, 1109.15, 1218.09, 1254.01, 1370.09, 1725.03, 2859.8, 2887.95, 2952.33, 3017.48

Mass: Base m/e=75 other m/e: 231, 171, 129, 117, 105, 97, 79, 75, 67, 59

Elemental analysis: calculated for $C_{14}H_{28}O_4Si$ : C, 58.33%; H, 9.72%;. Found: C, 58.15%; H, 10.20%;.

Specific rotation $[\alpha]_D$=–4.8 (c 1, CHCl$_3$) e.e. >95%

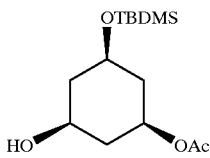

EXAMPLE 4

Preparation of 3-oxo-5-(tert.butyldimethylsilyloxy)-(1S, 5S)-cyclohexylacetate (6)

Cis,cis-3-(methylcarbonyloxy)-5-(tert.butyldimethylsilyloxy)-(1S,3R,5R)-cyclohexylacetate (5, 1.40 parts, 2.78 mmol) was dissolved in dichloromethane 5 parts) to the solution sodium acetate (0.1 part) and pyridinium chlorochromate (1.57 parts, 7.3 mmol) were added. The mixture was stirred for 5 hr at RT. Residue was extracted with ether (3×10 parts). Organic extracts were combined, filtered through ceilite. Filtrate was washed with brine:water (1:1), finally with brine. Organic layer was dried on anhydrous sodium sulphate and concentrated under vacuum. Residue was filtered through silica gel column to afford 3-oxo-5-(tert.butyldimethylsilyloxy)-(1S, 5S)-cyclohexylacetate 6 (1.30 parts, 93.5%).

1H NMR (CDCl$_3$): δ0.10 (d, 9H), 0.88 (d, 6H), 2.06 (s, 3H), 2.45 (m, 4H), 2.70 (m,2H), 4.00 (m, 1H), 5.00 (m, 1H)

13C NMR (CDCl$_3$): δ–4.95, 17.82, 20.97, 25.57, 39.34, 45.93, 50.30, 65.98, 67.23, 169.87, 205.27

IR (CHCl$_3$): 442.57, 756.83, 1218.50, 1244.99, 1723.00, 2857.44, 2932.80, 2953.64, 3019.98

Mass: Base m/e=163 other m/e: 185, 169, 145, 127, 117, 111, 101, 95, 75, 59

Elemental analysis: calculated for $C_{14}H_{26}O_4Si$: C, 58.74%; 9.09%. Found: C, 58.60%; H, 9.8%;.

Specific rotation $[\alpha]_D$=–11.54 (c 1, CHCl$_3$)

EXAMPLE 5

Preparation of 3-hydroxy-5-(tert-butyldimethylsilyloxy)-(3R,5S)-cyclohexan-1-one 7

3-Oxo-5-(tert.butyldimethylsilyloxy)-(1S, 5S)-cyclohexylacetate (6, 1.2 parts, 4.2 mmol) was dissolved in DMSO (10 parts) and 0.1 M phosphate buffer (pH 6.5, 90 parts). To the mixture, PLE (0.1 parts) was added and the reaction mixture was stirred for 48 hr at room temperature. It was filtered through ceilite and filtrate was extracted with ethyl acetate (3×100 parts). Organic extracts were combined and washed with brine. Organic layer was dried on anhydrous sodium sulphate and concentrated under vacuum. Residue was chromatographed on silica gel to afford 3-hydroxy-5-(tertbutyldimethylsilyloxy)-(3R,5S)-cyclohexan-1-one 7 (0.77 parts, 75%).

1H NMR (CDCl$_3$): δ0.08 (s, 6H), 0.85 (s, 9H), 1.95–2.4 (m, 2H), 2.45–2.78 (m, 4H), 3.96 (bs, 1H), 4.37 (m, 1H), 4.56 (m, 1H)

13C NMR (CDCl$_3$): δ–5.28, –5.50, 17.55, 25.34, 38.24, 49.56, 49.89, 68.86, 70.48, 206.78

IR (CHCl$_3$): 668.15, 759.18, 837.70, 1216.14, 1255.02, 1676.48, 1712.47, 2930.89, 2955.00, 3018.43, 3387.52, 3406.91

Mass: Base m/e=75 other m/e: 187, 169, 145, 129, 101, 95, 75, 69, 59

Elemental analysis: calculated for $C_{12}H_{24}O_3Si$ : C, 59.01%; H, 9.83%;. Found : C, 59.1%; H, 9.98%;.

Specific rotation $[\alpha]_D$=–22.06 (c 1, CHCl$_3$)

EXAMPLE 6

Preparation of 6-hydroxymethyl-4-(tert-butyldimethylsilyloxy)-(4S,6R)-tetrahydro-2H-2-pyranone (1)

3-Hydroxy-5-(tert-butyldimethylsilyloxy)-(3R,5S)-cyclohexan-1-one (7, 0.1 part, 0.394 mmol) and 50% 3-chloroperbenzoic acid (0.275 parts, 0.79 mmol) were mixed and kept in dark for 24 hr. Reaction mixture was dissolved in ethyl acetate and washed successively with sodium metabisulfite solution, sodium bicarbonate solution followed by brine wash. It was then dried on anhydrous sodium sulfate and solvent was removed under vacuum. Residue was purified by flash column chromatography to yield white, crystalline 6-hydroxymethyl-4-(tert-butyldimethylsilyloxy)-(4S,6R)-tetrahydro-2H-2-pyranone (1, yield 0.035 part, 50%).

1H NMR (CDCl$_3$): δ0.09, 0.07 (2s, 6H), 0.89 (s, 9H), 1.55–2.00(m+bs, 2H), 2.60 (d, 2H, J=3), 3.66 (dd, 1H, J=3, 12), 3.90 (dd, 1H, J=3, 12), 4.38 (m, 1H), 4.80 (m, 1H)

13C NMR (CDCl$_3$): δ–5.17, 17.66, 25.41, 32.59, 39.90, 63.24, 64.19, 76.73, 170.1

IR (CHCl$_3$): 666.31, 898.12, 1021.88, 1061.06, 1086.17, 1118.98, 1390.84, 1463.17, 1729.43, 2857.28, 3418.25

Mass: Base m/e=101 other m/e: 261, 229, 203, 185, 161, 143, 129, 111, 75, 68, 59

Elemental analysis: calculated for $C_{12}H_{24}O_4Si$: C, 55.38%; H, 9.20%;. Found C, 55.40%; H, 9.30%;.

Specific rotation $[\alpha]_D$=–1.96 (c 1, CHCl$_3$) e.e. 99% (determined by chiral HPLC of corresponding benzoate derivative, column-Whelk-O1 [4.0 mm Id×25 cm] AT-256; λ=254 nm, flow rate: 1 ml/min; mobile phase: hexane:isopropanol 92:08; retention time for benzoate of 1=20.10, for benzoate of ent-1=17.48).

We claim:

1. A process for the preparation of 6-Hydroxy methyl-4-(tert-butyl dimethylsilyloxy)-(4R,6S)-tetra hydro 2H-2-pyranone of formula 1 which comprises a) reacting 3-hydroxy-5-(tert.butyldimethylsilyloxy)-(1S,3R,5R)-cyclohexylacetate having formula 5,

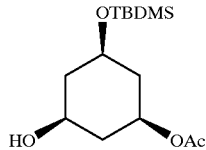

in an organic solvent with chlorochromate of tertiary amines at temperature ranging from 10° C. to 30° C., quenching the reaction by adding diethyl ether, filtering the mixture through celite and washing with brine, removing the solvent by evaporation, followed by fast column filtration to obtain 3-oxo-5-(tert.butyldimethylsilyloxy)-(1S,5S)-cyclohexylacetate having formula 6,

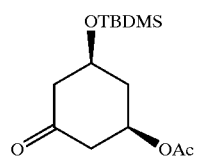

b) hydrolysing 3-oxo-5-(tert.butyldimethylsilyloxy)-(1S,5S)-cyclohexylacetate having formula 6 with lipase enzyme in a buffer having pH range of 5 to 7, at a temperature ranging from 25 to 30° C. for a period ranging between 24 to 48 hr, extracting the mixture with an organic solvent, removing the solvent by evaporation and on column chromatography to obtain 3-hydroxy-5-(tert-butyldimethyl silyloxy)-(3R,5S)-cyclohexan-1-one having formula 7,

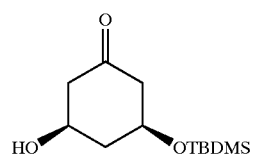

and c) reacting 3-hydroxy-5-(tert-butyldimethyl silyoxy)-(3R,5S)-cyclohexan-1-one having formula 7 with m-chloroperbenzoic acid at room temperature for the period ranging from 16–24 hours, extracting with organic layer, washing with sodium metabisulphite, brine, drying and on evaporation to obtain 6-hydroxymethyl-4-(tertbutyldimethylsilyloxy)-(4S,6R)-tetrahydro-2H-2-pyranone having formula 1

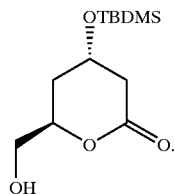

2. A process as claimed in claim 1, wherein the organic solvent used in steps a–c for the extraction of the product is selected from the group consisting of ethyl acetate, chloroform and dichloromethane.

3. A process as claimed in claim 1, wherein the buffer used in steps b for the reaction is selected from phosphate buffer and citrate buffer.

4. A process as claimed in claim 1, wherein the lipase used in steps b for the reaction is selected from the group consisting from pig procain lipase (PPL), pig liver esterase (PLE) and chicken liver acetone powder (CLAP).

5. A process as claimed in claim 1, wherein the enzymatic hydrolysis used in step b is mild and suppresses B-elimination along with enhancement in optical purity.

6. A process as claimed in claim 1, wherein the oxidising agent used is selected from the group consisting of chloroperbenzoic acid, hydrogen peroxide and per acetic acid.

7. A compound 3-oxo-5-(tert.butyldimethylsilyloxy-(1S,5S)-cyclohexylacetate having formula 6:

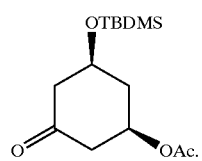

8. A compound 3-hydroxy-5-(tert.butyldimethylsilyloxy)-(3R,5S)-cyclohexan-1-one having formula 7

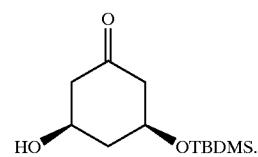

9. The process according to claim 1, wherein the organic solvent is a chloroalkane.

* * * * *